United States Patent [19]

Yokoyama et al.

[11] Patent Number: 4,617,821

[45] Date of Patent: Oct. 21, 1986

[54] GAS DETECTING DEVICE

[75] Inventors: Meiso Yokoyama; Makoto Takahashi; Tsunehiko Nishiwaki; Makoto Imai, all of Nagaoka, Japan

[73] Assignee: Nippon Seiki Co., Ltd., Niigata, Japan

[21] Appl. No.: 701,217

[22] Filed: Feb. 13, 1985

[30] Foreign Application Priority Data

Feb. 24, 1984 [JP] Japan .............................. 59-26233[U]
Feb. 25, 1984 [JP] Japan .............................. 59-26566[U]
Mar. 24, 1984 [JP] Japan .............................. 59-42476[U]

[51] Int. Cl.$^4$ ........................................... G01N 31/00
[52] U.S. Cl. ......................................... 73/23; 362/253
[58] Field of Search ................. 73/23, 27 R; 128/719; 362/253, 208, 96; 340/632, 633, 634; 422/84, 98

[56] References Cited

U.S. PATENT DOCUMENTS

| | | | |
|---|---|---|---|
| 3,877,291 | 4/1975 | Hoppesch et al. | 73/27 R |
| 3,903,726 | 9/1975 | Hirosawa et al. | 73/23 |
| 4,047,893 | 9/1977 | Kok et al. | 422/84 |
| 4,090,078 | 5/1978 | Heim | 250/343 |
| 4,432,041 | 2/1984 | Pfisterer et al. | 362/253 |

Primary Examiner—Stephen A. Kreitman
Attorney, Agent, or Firm—Lowe Price LeBlanc Becker & Shur

[57] ABSTRACT

A gas detecting device principally used for detecting liquor contained in expired gas of a driver of a car. The gas detecting device is of the type wherein an inlet opening for sucking expired gas of an object person for measurement is provided adjacent an end of a cylindrical member, and an air blower for attracting the expired gas thus sucked and a gas detecting element for detecting liquor in the expired gas are contained in said cylindrical member, and comprises an illuminating section connected to said power source for illuminating forwardly of said inlet opening of said cylindrical member. Thus, the gas detecting device is integrally provided with an illuminating function and a gas detecting function. The device may further comprise a convex lens located forwardly of the illuminating section for condensing light irradiated from the illuminating section whereby it is provided with a distance setting function for setting a distance between the object person for measurement and the gas detecting device in addition to the aforementioned two functions. The device may further comprise a switch having a movable contact connected to the power source, a first fixed contact connected to a light source of the distance setting section, and a second fixed contact connected to a heater contained in the detecting element whereby power consumption can be saved.

5 Claims, 5 Drawing Figures

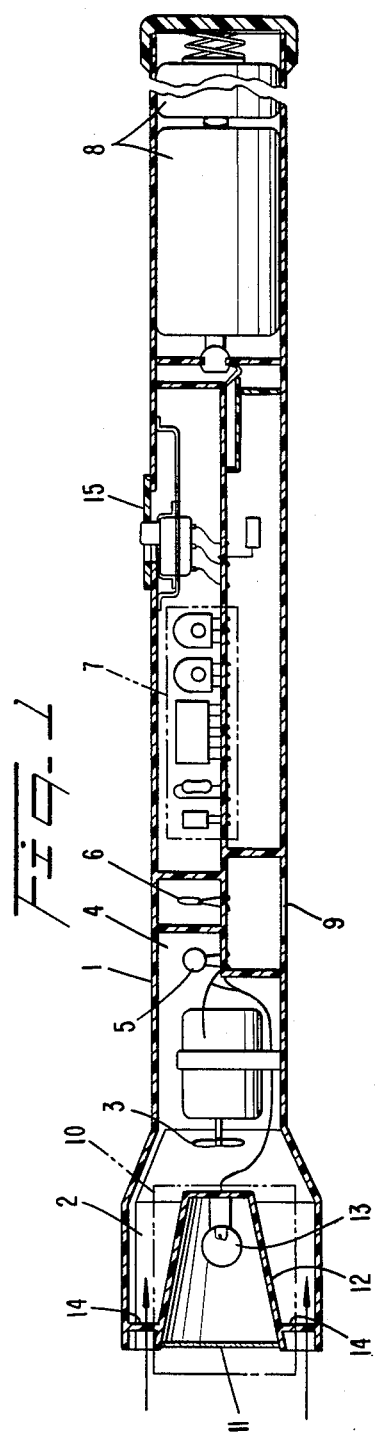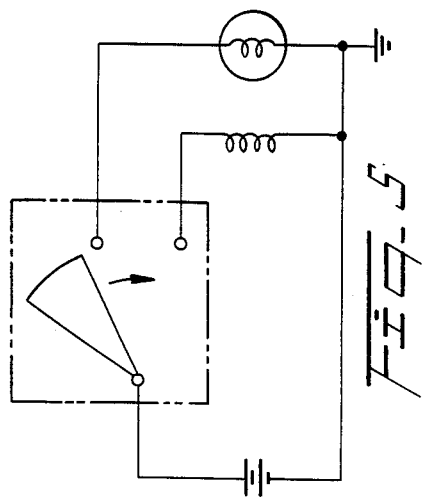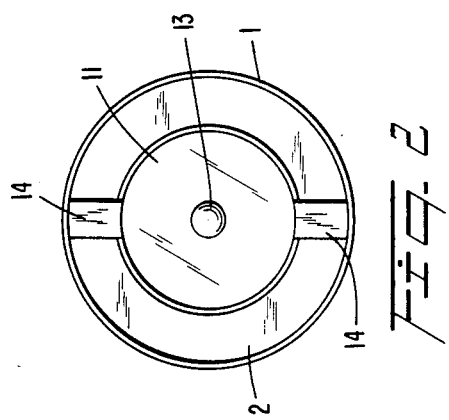

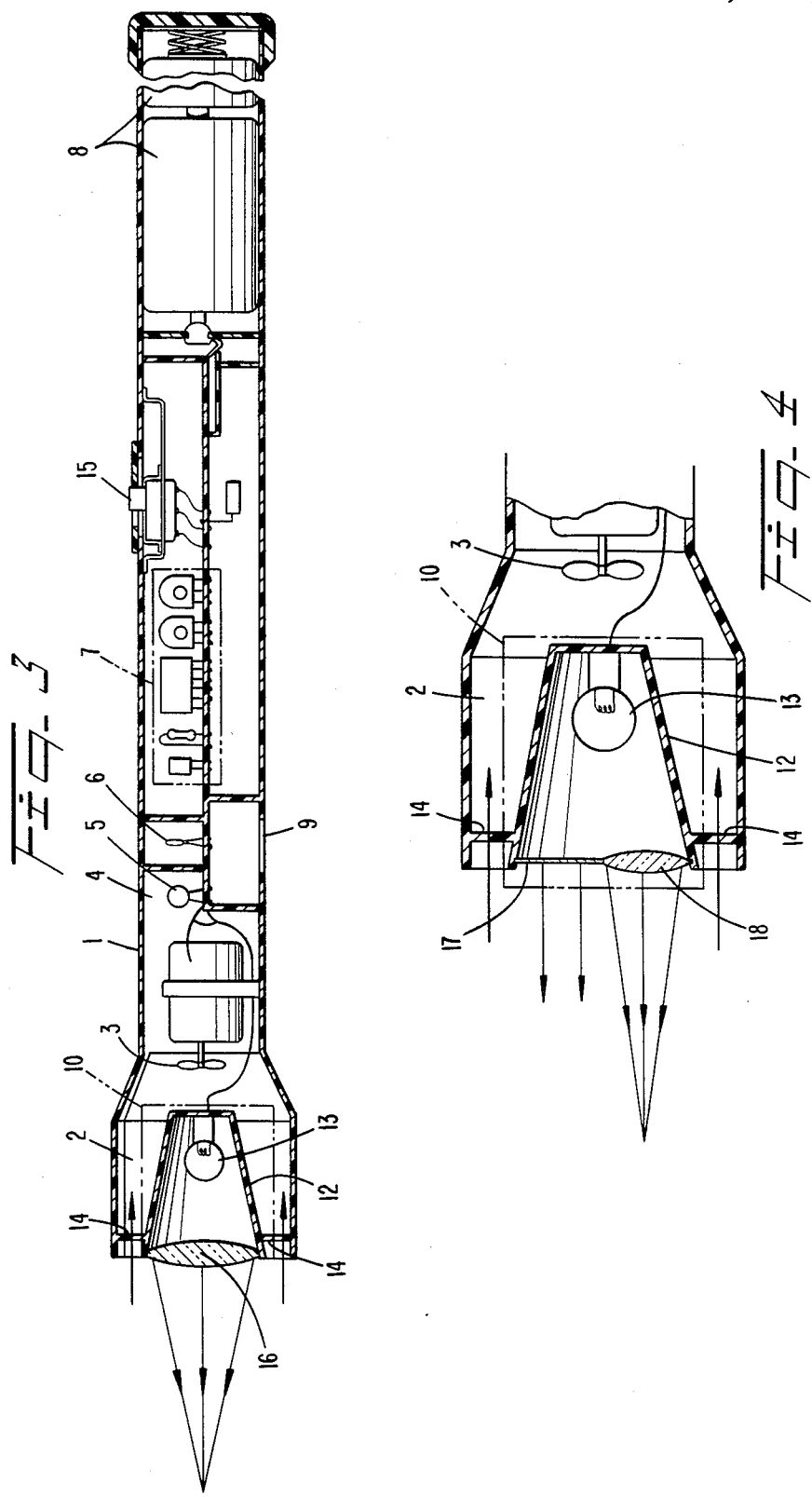

GAS DETECTING DEVICE

BACKGROUND OF THE INVENTION

1. Field of the Invention

This invention relates to a gas detecting device principally for detecting liquor contained in expired gas of a vehicle operator.

2. Description of the Prior Art

A gas detecting device of the type wherein expired gas of a driver of a car such as an automobile or a motorcycle is positively taken in and an indicator lamp is controlled to be lit up by a detecting circuit in response to a change in electric conductivity of a gas detecting element made of a semiconductor and provided in the detecting circuit in accordance with a well known semiconductor characteristic reaction of the detecting element itself when the expired gas taken into the device is contacted with the gas detecting element in order to facilitate detection of liquor present in the expired gas taken into the device, is disclosed, for example, in Japanese Publication Utility Model No. 52-35759.

According to the gas detecting device, a volume in the detecting circuit is adjusted, prior to forwarding or shipment of the device, at an inspection stage of production steps such that the indicator lamp may be lit up when the device is positioned at a point spaced a predetermined distance (normally at a point spaced by a distance from 15 to 20 cm) from test alcohol of a predetermined fixed concentration.

Accordingly, it is desirable that the gas detecting device is spaced, in actual use thereof, by such a distance as described above from a mouth of an object person for measurement who is a driver of a car.

However, the gas detecting device is used, in most cases, particularly outdoors at night, and actually a measurer holds the gas detecting device in one hand and an illuminating device such as a flash-light in the other hand to illuminate a mouth of an object person for measurement in order to set a distance to the gas detecting device. According to the gas detecting device, if measurement is not accomplished at a position of the aforementioned predetermined distance, the sensitivity of the detecting element will vary accordingly, resulting in possible errors in measurement. Thus, it is troublesome for the measurer to make measurement while he holds a gas detecting device and an illuminating device in both hands, and it is difficult for him to always make accurate measurement since both hands are occupied.

Meanwhile, setting of the distance from an object person for measurement and the gas detecting device must rely upon eye measurement of a measurer. Consequently, a difference in setting of a distance will vary the sensitivity of the gas detecting element, resulting in possible errors in measurement, and thus setting of a distance is troublesome to a measurer who must always attain accurate measurement.

In addition, since the gas detecting device must necessarily be used in an appropriate atmosphere, for example, to remove deviations of operating characteristics caused by the temperature in order to attain stabilized measurement, generally a heater within the detecting element of the gas detecting device is energized so that the gas detecting device may be operated at a relatively high temperature. Accordingly, the heater normally requires a relatively large electric current, and hence exhaustion of a power source at an early stage cannot be avoided by large power consumption. Since such gas detecting devices are used for a long time particularly outdoors at night, in most cases they are of the portable type and employ dry cells as a power source. Accordingly, large power consumption is required for heating with a heater and hence will cause exhaustion of such cells at an early stage so that before such exhaustion of cells is noticed, measurement may possibly be performed. Thus, the gas detecting device is disadvantageous in its reliability.

SUMMARY OF THE INVENTION

It is a first object of the present invention to provide a gas detecting device which also has functions as an illuminating device in order to facilitate operations for measuring the smell of liquor.

It is a second object of the invention to provide a gas detecting device which facilitates setting of a distance between an object person for measurement and the gas detecting device itself so as to maintain constant the distance from each object person for measurement to the device to always attain accurate measurement.

It is a third object of the invention to provide a gas detecting device wherein power consumption by a heater within a gas detecting element is saved to elongate the life of cells thereby to improve the reliability of measurement by the device.

The above and other objects, features and advantages of the present invention will become apparent from the following description when taken in conjunction with the accompanying drawings in which preferred embodiments of the present invention are shown by way of illustrative example, and like reference characters designate like parts throughout.

BRIEF DESCRIPTION OF THE DRAWINGS

FIG. 1 is a sectional view illustrating an embodiment of a gas detecting device according to the present invention;

FIG. 2 is a front elevational view of the device of FIG. 1;

FIG. 3 is a sectional view illustrating another embodiment of the invention;

FIG. 4 is a sectional view illustrating a further embodiment of the invention; and FIG. 5 is an electric circuit diagram illustrating a wiring of slide switches for a gas detecting device according to the invention.

DETAILED DESCRIPTION OF THE PREFERRED EMBODIMENTS

Reference is first had to FIG. 1 which is a sectional view illustrating a first embodiment of a gas detecting device according to the present invention and also to FIG. 2 which is a front elevational view of the device of FIG. 1.

The gas detecting device includes a cylindrical member 1 made of a pipe of a resin material or the like and having a diameter of about 5 cm. The cylindrical member 1 has, adjacent a forward end thereof, an inlet opening 2 for introducing expired gas from an object person for measurement into the gas detecting device. The cylindrical member 1 contains inside thereof an air blower 3 located rearwardly of the inlet opening 2 for sucking expired gas from an object person for measurement into the device, a gas detecting element 5 located in a ventilating path 4 behind the air blower 3 and made of a semiconductor of metal oxides such as $SnO_2$, $ZnO_2$, ZnO, Fe$_2$O$_3$, and so on, an indicator lamp 6 formed from a light emitting diode or the like which lights when the smell of liquor is detected, a detecting circuit 7, and a power source 8 formed from dry cells or the like. The air blower 3, detecting element 5, indicator lamp 6, detecting circuit 7 and power source 8 are electrically connected in circuit. The cylindrical member 1 has an air hole 9 formed at a suitable position in a circumferential wall thereof. The air hole 9 serves as an outlet hole for the ventilating path 4.

An illuminating section 10 is provided at a central portion of the inlet opening 2 and includes a light source 13 formed from a small bulb or the like and disposed within a space which is defined by a flat lens 11 and a substantially conical reflecting plate 12. The illuminating section 10 is contained in the cylindrical member 1 and is secured to a mounting plate 14 in the inlet opening 1 such that a beam of light emitted from the light source 13 may be passed through the flat lens 11 and irradiated forwardly of the inlet opening 2. The illuminating section 10 is electrically connected to the power source 8. A switch 15 is interposed between the light source 13 and so on and the power source 8.

Description will now be given of operations of the embodiment having such constructions as described above.

At first, if the light source 13 of the illuminating section 10 of the gas detecting device is lit up by a measurer, a beat of light from the light source 13 is reflected by tne reflecting plate 12 and then passes through the flat lens 11 and is irradiated forwardly of the inlet opening 2 of the gas detecting device. The light beam illuminates mouth of an object person for measurement, and then after the gas detecting device is moved to effect setting of the distance to the object person for measurement, expired gas of the object person for measurement is sucked into the gas detecting device from the inlet opening 2. The expired gas thus sucked is attracted to the detecting element 5 by the air blower 3 to effect required measurement, and if liquor is contained beyond a predetermined level in the expired gas, the indicator lamp 6 is lit up.

In this manner, a complicated operation for setting a distance from a gas detecting device to a mouth of an object person for measurement, which must be done, with a conventional gas detecting device, while with the gas detecting device and an illuminating device held by the object person for measurement, the illuminating device is suitably oriented to irradiate light properly forwardly of an inlet opening of the gas detecting device, can be effected, with the gas detecting device according to the present invention, by holding and moving only the gas detecting device since light can always be irradiated forwardly of the inlet opening owing to the arrangement in which the illuminating section is integrally installed in the gas detecting device and thus irradiates light forwardly of the inlet opening of the device. This facilitates a distance setting operation and improves accuracy in measurement of the device since a measuring operation can be effected with a fixed distance maintained.

While an embodiment of the present invention has been described in detail, the invention naturally includes various variations within a spirit and a scope thereof.

For example, while in the embodiment described the flat lens 11 is located adjacent an opening of the cylindrical member 1, the flat lens 11 may otherwise be located forwardly or rearwardly of the cylindrical member 1. Further, where the cylindrical member 1 is made thin, the illuminating section 10 may otherwise be securely mounted outside the cylindrical member 1.

Besides, while the lens 11 is formed as a flat lens, a concave lens, a convex lens or the like may be used instead for the lens 11 if light can be irradiated forwardly of the inlet opening.

As apparent from the foregoing description, according to the present invention, a gas detecting device of the type wherein an inlet opening for sucking expired gas of an object person for measurement is provided adjacent an end of a cylindrical member, and an air blower for attracting the expired gas thus sucked and a detecting element for detecting liquor in the expired gas are contained in the cylindrical member, comprises an illuminating section for illuminating forwardly of the inlet opening of the cylindrical member. Due to this arrangement, the gas detecting, device has an illuminating function together with a gas detecting function, and hence a measurer can accomplish an illuminating operation and a gas detecting operation using only hand. Accordingly, an operation for setting a distance between an object person for measurement and the gas detecting device can be made easily, and since a measuring operation is effected while the distance is maintained fixed, accuracy in measurement can possibly be improved.

Referring now to FIG. 3 which is a sectional view showing a second embodiment of a gas detecting device according to the present invention, like parts or components are designated by like reference numerals to those of FIGS. 1 and 2 and detailed description thereof is omitted herein. An illuminating section 10 having a distance setting function is located at the center of an inlet opening 2. The illuminating section 10 includes a light source 13 formed from a small bulb or the like disposed within a room which is defined by a substantially conical reflecting plate and a condensing convex lens 16 located at a forward opening of the reflecting plate 12 and having a local distance as hereinafter described. The convex lens 16 is provided in place of the flat lens 11 (FIGS. 1 and 2). The illuminating section 10 is securely mounted on a mounting plate 14 in the inlet opening 2 such that a beam of light emitted from the light source 13 may pass through the convex lens 16 and be irradiated forwardly of the inlet opening 2. The illuminating section 10 is electrically connected to a power source 8. The convex lens 16 has such a focal distance that light is condensed at a mouth of an object person for measurement when the inlet opening 2 of the gas detecting device is spaced from the object person for measurement by a predetermined fixed distance which is determined at an inspection stage of such production steps as described hereinabove.

Now, description will be given of operations of the present embodiment having such construction as described above.

A user of the gas detecting device first lights up the light source 13 of the illuminating section 10 of the device and adjusts a distance from an object person for measurement to the device such that light irradiated through the convex lens 16 may be condensed at a mouth of the object person for measurement, and then the gas detecting device is secured at the adjusted position. Then, expired gas of the object person for measurement is sucked into the gas detecting device through the inlet opening 2. The expired gas thus sucked is attracted to a detecting element 5 by an air blower 3 and is measured thereby. If liquor is contained more than a predetermined level, an indicator lamp 6 will be lit up.

In this manner, since the gas detecting device is provided with the illuminating section 10 for setting a distance from an object person for measurement to the gas detecting device by moving the gas detecting device so that light from the light source 13 may be condensed by the convex lens 16, the distance is maintained constant to any of object persons for measurement. Accordingly, accuracy in measurement is improved to eliminate errors in measurement. Besides, measuring operations can be effected easily only by moving the gas detecting device to determine the distance so as to condense light.

While the second embodiment of the present invention has been described in detail, the invention naturally includes various variations within a spirit and a scope thereof.

For example, while in the embodiment described the convex lens 16 is located adjacent an opening of the cylindrical member 1, the convex lens may otherwise be located forwardly of the cylindrical member 1. Further, where the cylindrical member 1 is made thin, the illuminating section 10 may otherwise be securely mounted outside the cylindrical member 1.

Further, while the convex lens 16 has a same diameter as the diameter of the opening of the substantially conical reflecting plate 12, if otherwise a convex lens section 18 having a smaller diameter is formed at a portion of a flat lens 17 having a same diameter as the diameter of the opening of the reflecting plate 12 as shown in FIG. 4, light passing through the convex lens section 18 will be condensed at a position of a focal distance of the convex lens section 18 while light passing through the flat lens 17 will become a parallel light beam which will irradiate remotely. Accordingly, the gas detecting device may serve as an ordinary flashlight and hence is convenient for use at night. In this case, a colored member may be applied to a surface of the convex lens section 18 in order that light passing through the convex lens section 18 may be clearly distinguished from light passing through the other part so as to make setting of the distance easier. Meanwhile, the power source 8 may otherwise be accommodated in another box than the cylindrical member 1 or else be a battery of a car.

As apparent from the foregoing description, according to the present invention, a gas detecting device of the type wherein an inlet opening for sucking expired gas of an object person for measurement is provided adjacent an end of a cylindrical member, and an air blower for attracting the expired gas thus sucked and a detecting element for detecting liquor in the expired gas are contained in the cylindrical member, comprises an illuminating section having a distance setting function and including a light source, a reflecting plate for reflecting light from the light source, and a convex lens for condensing light reflected from the reflecting plate. Accordingly, an operation for setting a distance between an object person for measurement and the gas detecting device can be made easily, and the distance can be maintained constant for any of object persons for measurement. Consequently, measurement can be effected always is accuracy.

Referring to FIG. 5 which is an electric circuit diagram of essential part showing a third embodiment of a gas detecting device according to the present invention, the present embodiment is devised based upon the first embodiment as illustrated in FIGS. 1 and 2 or the second embodiment as illustrated in FIGS. 3 and 4, and like parts or components are designated by like reference numerals to those of the preceding embodiments and detailed description thereof will be omitted herein. It is to be noted that construction of those parts of reference numerals not shown in FIG. 5 similar to that of any of FIGS. 1 to 4.

A slide switch 15 is provided on a circumferential face of a cylindrical member 1 so as to be exposed outside and is adapted to control an electric current to a light source 13 and a heater 5A within a detecting element 5. The slide switch 15 has a movable contact 15A constantly held in contact with the power source 8, a first fixed contact 15B connected to the light source 13, and a second fixed contact 15C connected to the detecting element 5 and the heater 5A. If the movable contact 15A is moved to the first fixed contact 15B, the light source 13 is energized, and alternatively if the movable contact 15A is moved to the second fixed contact 15C, the light source 13 and the heater 5A are both energized.

Operations of the embodiment having such a construction as described just above will be described below.

In most cases, a gas detecting device is used outdoors particularly at night, and in such a situation, setting of the distance from an object person to the gas detecting device must rely upon eye measurement by a measurer. Accordingly, the sensitivity of a detecting element 5 varies depending upon different settings of the distance, resulting in possible errors in measurement. Besides, such a setting operation of the distance is troublesome to a measurer who must always attain accurate measurement.

Thus, a measurer first moves the movable contact 15A of the slide switch 15 to the first fixed contact 15B to light up the light source of the illuminating section 10. Then, after the distance between a mouth of an object person for measurement and the gas detecting device is determined, the movable contact 15A of the slide switch 15 is moved to the second fixed contact 15c to allow an electric current to be supplied to the heater 5A of the detecting element 5. Expired gas is then taken into the gas detecting device through the inlet opening 2 and is sucked to the detecting element 5 by the air blower 3 so that measurement may be effected by the same. If liquor is contained more than a predetermined level, the indicator lamp 6 is lit up.

If the slide switch 15 is turned off after completion of the measurement, the light source 13 and the heater 5A are deenergized, and hence consumption of the power source 8 is prevented. Further, since time is required more or less during setting of the distance, if the heater 5A is energized after setting of the distance using the slide switch 15 having two switching positions as in the present embodiment, rapid consumption of the power source 8 can be prevented thereby. This is because consumption of the power source 8 by the heater 5A is particularly high. This solution is particularly effective for a portable gas detecting device in which a dry cell is employed for the power source.

In this manner, since the present embodiment includes the slide switch 15 having two switching positions so as to allow the light source 13 and the heater 5A causing high consumption of the power source 8 to be energized for a necessary period of time, there is no need of replacement of the power source 8 for a long period of time, resulting in improvement in reliability in measurement.

While the third embodiment of the present invention has been described in detail, the invention naturally includes various variations within a spirit and a scope thereof.

For example, while the present embodiment employs a slide switch having two switching positions, a different switch may otherwise be employed if it has of the type which has two switching positions.

Further, while in the embodiment the power source 13 and the heater 5A are both energized when the movable contact 15A is moved to the second fixed contact 15C, another construction is also allowable wherein only the heater 5A is energized then.

As apparent from the foregoing description, according to the present invention, a gas detecting device of the type wherein an inlet opening for sucking expired gas of an object person for measurement is provided adjacent an end of a cylindrical member, and an air blower for attracting the expired gas thus sucked and a detecting element for detecting liquor in the expired gas are contained in the cylindrical member, comprises an illuminating section for irradiating light from a light source forwardly of the inlet opening of the cylindrical member, and a switch having movable contact connected to a power source, a first fixed contact connected to the light source of the illuminating section, and a second fixed contact connected to a heater contained in the detecting element. Due to this arrangement, the gas detecting device can save power consumption by the heater contained in the detecting element, thereby elongating the life of cells and improving the reliability in measurement.

What is claimed is:

1. In a gas detecting device including a cylindrical member formed with an inlet opening through which exhalation gas of a person to be tested for alcohol level enters said cylindrical member, and an air blower for drawing the exhalation gas towards a gas detecting element contained in said cylindrical member and connected to a power source, the improvement which comprises an illuminating section located inside said cylindrical member and connected to said power source for providing illumination forwardly of said inlet opening of said cylindrical member, wherein said illuminating section includes a light source, a substantially conical reflecting plate for reflecting light from said light source, said reflecting plate having a forward opening through which light passes from the light source to illuminate the mouth of a person for measurement of exhalation gas with said gas detecting device spaced from the person in alignment with the mouth of said person by means of light from said light source.

2. A gas detecting device according to claim 1, further comprising a switch having a movable contact connected to said power source, a first fixed contact connected to said light source, and a second fixed contact connected to a heater contained in said detecting element, said power source also being contained within the cylindrical member.

3. In a gas detecting device including a cylindrical member formed with an inlet opening through which exhalation gas of a person to be tested for alcohol level enters said cylindrical member, and an air blower for drawing the exhalation gas towards a gas detecting element contained in said cylindrical member and connected to a power source, the improvement which comprises an illuminating section connected to said power source for providing illumination forwardly of said inlet opening of said cylindrical member, wherein said illuminating section includes a light source, a substantially conical reflecting plate for reflecting light from said light source, said reflecting plate having a forward opening, and a lens provided in the forward opening of said reflecting plate, wherein said lens in a convex lens having a focal distance such that said lens condenses light from said light source at the mouth of the person for measurement when said gas detecting device is spaced from the person for measurement by a distance determined at an inspection stage during production.

4. In a gas detecting device including a cylindrical member formed with an inlet opening through which exhalation gas of a person to be tested for alcohol level enters said cylindrical member, and an air blower for drawing the exhalation gas towards a gas detecting element contained in said cylindrical member and connected to a power source, the improvement which comprises an illuminating section connected to said power source for providing illumination forwardly of said inlet opening of said cylindrical member, wherein said illuminating section includes a light source, a substantially conical reflecting plate for reflecting light from said light source, said reflecting plate having a forward opening, and a lens provided in the forward opening of said reflecting plate, wherein said lens is a flat lens having at a part thereof a convex lens section which has a focal distance such that said lens condenses light from said light source at the mouth of the person for measurement when said gas detecting device is spaced from the person for measurement by a distance determined at an inspection stage during production.

5. A gas detecting device according to claim 4, wherein said convex lens section of said flat lens has a coloring member provided thereon which colors light passing through said convex lens section in a different color than a color of light which passes through the other part of said flat lens.

* * * * *